United States Patent [19]

Kitahara et al.

[11] 4,440,621
[45] Apr. 3, 1984

[54] SYSTEM FOR DETECTION OF AIR/FUEL RATIO IN IC ENGINE BY USING OXYGEN SENSOR OPERATED WITH SUPPLY OF CURRENT

[75] Inventors: Tsuyoshi Kitahara, Yokohama; Masaaki Uchida, Yokosuka; Kohki Sone, Tokyo, all of Japan

[73] Assignee: Nissan Motor Company, Ltd., Yokohama, Japan

[21] Appl. No.: 446,315

[22] Filed: Dec. 2, 1982

[30] Foreign Application Priority Data

[JP] Japan ...............................

[51] Int. Cl.³ ............................................. G01N 27/58
[52] U.S. Cl. ..................................... 204/406; 60/276; 123/489; 204/425
[58] Field of Search ........................ 204/406, 425, 1 S; 123/489; 60/276

[56] References Cited

U.S. PATENT DOCUMENTS 4,366,039 12/1982 Uchida et al. ....................... 204/406

FOREIGN PATENT DOCUMENTS

2083629 3/1982 United Kingdom ................ 204/406

Primary Examiner—G. L. Kaplan
Attorney, Agent, or Firm—Schwartz, Jeffery, Schwaab, Mack, Blumenthal & Koch

[57] ABSTRACT

An air/fuel ratio detection system for an IC engine, using an oxygen sensor element of the concentration cell type which has a laminate of a measurement electrode layer exposed to the exhaust gas, a porous layer of oxygen ion conductive solid electrolyte and a reference electrode layer and requires the supply of a small DC current thereto to produce a reference oxygen partial pressure at the reference electrode by a balance between migration of oxygen ions to the reference electrode and diffusion of oxygen molecules therefrom. To prevent excessive rise in the reference oxygen partial pressure even when the engine continues to discharge exhaust gas high in the content of oxygen, the detection system has a control circuit which controls the intensity and flow direction of the current for the sensor element with reference to a voltage which is produced by adding a definite voltage to, or subtracting the definite voltage from, the sensor output voltage depending on the level of oxygen content in the exhaust gas indicated by the sensor output voltage and smoothing the voltage resulting from the addition or subtraction.

9 Claims, 11 Drawing Figures

SYSTEM FOR DETECTION OF AIR/FUEL RATIO IN IC ENGINE BY USING OXYGEN SENSOR OPERATED WITH SUPPLY OF CURRENT

BACKGROUND OF THE INVENTION

This invention relates to a system for detecting actual air/fuel ratio in an internal combustion engine by using an oxygen sensor in the exhaust gas, the oxygen sensor being of the concentration cell type requiring the supply of a small DC current thereto for the purpose of producing and maintaining a reference oxygen partial pressure therein.

In recent internal combustion engines and particularly in automotive engines, it is prevailing to control the air/fuel mixing ratio precisely to a predetermined optimum value by performing feedback control with a view to improving the efficiencies of the engine and reducing the emission of noxious or harmful substances. In the current feedback control systems for this purpose it is usual to produce a feedback signal indicative of the air/fuel ratio of an air-fuel mixture actually supplied to the engine by sensing the concentration of oxygen in the exhaust gas since there is a determined relationship between the air/fuel ratio in the engine and the oxygen content in the exhaust gas. In many cases the target value of the air/fuel ratio under feedback control is a stoichiometric air/fuel ratio. For example, when a so-called three-way catalyst is used in the exhaust system to achieve reduction of NOx and oxidation of CO and HC simultaneously, the air/fuel ratio must be controlled precisely to a stoichiometric ratio because this catalyst exhibits highest conversion efficiencies in an exhaust gas produced by combustion of a stoichiometric air-fuel mixture.

As for the device to sense the oxygen concentration in the exhaust gas to thereby detect actual air/fuel ratio in the engine, it is usual to use an oxygen sensor of the concentration cell type having a layer of an oxygen ion conductive solid electrolyte such as zirconia containing a small amount of stabilizing oxide such as yttria, a measurement electrode layer formed porously on an outer side of the solid electrolyte layer and a reference electrode layer formed on the opposite side. In an oxygen sensor of this type it is necessary to maintain a reference partial pressure of oxygen on the reference electrode side of the solid electrolyte layer, and it is well known to expose the reference electrode layer to air as the source of reference partial pressure of oxygen by forming the solid electrolyte layer into a tubular shape. This oxygen sensor generates an electromotive force of which the magnitude depends on the difference between the partial pressure of oxygen in a gas coming into contact with the measurement electrode layer and the reference oxygen pressure at the reference electrode layer. In the exhaust gas of an internal combustion engine the output of this oxygen sensor exhibits a great and sharp change when the air/fuel ratio in the engine changes across the stoichiometric point because such a change in the air/fuel ratio results in a great change in the content of oxygen in the exhaust gas. However, the tubular shape of the solid electrolyte layer to expose only the reference electrode to air offers various problems such as low productivity of the oxygen sensor and difficulty in desirably reducing the size of the sensor.

Recently an advanced oxygen sensor of the concentration cell type has been developed as shown in U.S. Pat. No. 4,207,159 for example. The sensitive part or oxygen concentration cell of this oxygen sensor takes the form of a laminate of very thin layers, including a porous solid electrolyte layer and two electrode layers, supported on a plate-shaped ceramic substrate of very small size. As a feature of this sensor, a reference partial pressure of oxygen is produced and maintained in the laminated cell without using any extra oxygen source material by supplying a very small DC current to the cell so as to flow in the solid electrolyte layer between the two electrode layers. The flow of the current causes migration of oxygen ions in the solid electrolyte layer toward the reference electrode layer, and at this electrode the oxygen ions are converted to oxygen molecules, which gradually diffuse outward through the micropores in the solid electrolyte layer. Consequentially a nearly constant partial pressure of oxygen as a balance between the migration of oxygen ions and the outward diffusion of oxygen molecules is maintained at the reference electrode while the measurement electrode layer is exposed to an oxygen-containing gas subjected to measurement. In the exhaust gas, this oxygen sensor too exhibits a great and sharp change in the level of its output voltage in response to a change in the air/fuel ratio in the engine across the stoichiometric ratio, though it is also possible to modify the output characteristic of this oxygen sensor as shown in U.S. Pat. No. 4,224,113 for example.

This advanced oxygen sensor is advantageous in many respects such as quickness of response, smallness in size and high productivity and therefore has been increasingly put into industrial practice. However, there is the need to adequately control the current supplied to this oxygen sensor because the rate of diffusion of oxygen molecules in the porous solid electrolyte layer as a factor in producing the reference oxygen partial pressure varies depending on the temperature of and oxygen content in the exhaust gas and such properties of the exhaust gas are variable depending on the operating conditions of the engine. Particularly it is undesirable that the reference oxygen partial pressure becomes excessively high as the result of unbalance between the rate of supply of oxygen ions to the reference electrode layer by the action of the current and the rate of the outward diffusion of oxygen molecules, because there arises a possibility that the thin reference electrode layer or the laminated cell as a whole peels away from the ceramic substrate by the action of the excessively increased pressure of oxygen.

SUMMARY OF THE INVENTION

It is an object of the present invention to provide a system for detecting actual air/fuel ratio in an internal combustion engine by using an oxygen sensor of the above described concentration cell type requiring the supply of a DC current thereto to produce and maintain a reference oxygen partial pressure therein, in which system the current for operation of the oxygen sensor is controlled so as to maintain the reference oxygen partial pressure in the sensor nearly constant under varying operating conditions of the engine so that accurate detection of the air/fuel ratio can be continued without suffering from failure of the oxygen sensor.

An air/fuel ratio detection system according to the invention has an oxygen sensor element of the concentration cell type, which is disposed in an exhaust passage of the engine and has a laminate of a measurement electrode layer exposed to the exhaust gas, a microscopically porous layer of an oxygen ion conductive solid electrolyte and a reference electrode layer supported on a ceramic substrate, current supplying means for supplying a DC current to the sensor element to cause migration of oxygen ions in the solid electrolyte layer to thereby produce a reference oxygen partial pressure at the interface between the solid electrolyte layer and the reference electrode layer, and judgement means for producing an air/fuel ratio signal which indicates whether the air/fuel ratio is above or below the stoichiometric air/fuel ratio by comparing a signal voltage which is substantially proportional to output voltage of the sensor element with a reference signal. As the improvement according to the invention, the current supplying means comprises modification means for producing a modified voltage which is lower than the signal voltage by a predetermined value while the air/fuel ratio signal indicates that the air/fuel ratio in the engine is below the stoichiometric ratio but is higher than the signal voltage by the predetermined value while the air/fuel ratio signal indicates that the air/fuel ratio is above the stoichiometric ratio, smoothing means for smoothing the modified voltage to produce a smoothed voltage, and current control means for controlling the aforementioned DC current such that the DC current flows in the solid electrolyte layer of the sensor element from the reference electrode layer toward the measurement electrode layer and becomes smaller as the smoothed voltage becomes higher while the smoothed voltage is below a reference level, but flows in the reverse direction and becomes larger as the smoothed voltage becomes higher while the smoothed voltage is above the reference level.

In this air/fuel ratio detection system the smoothed voltage becomes above the reference level when the air/fuel ratio in the engine remains above the stoichiometric ratio and accordingly the concentration of oxygen in the exhaust gas remains high for a certain period of time. Then the flow of the DC current in the oxygen sensor element is inversed to thereby allow outward migration of oxygen ions from the reference electrode layer, while the intensity of the current is always controlled in dependence on the magnitude of the smoothed voltage. By this manner of control of the current for the sensor element, it is possible to surely prevent an undesirable rise in the reference oxygen partial pressure in the oxygen sensor element resulting from the supply of excessively large amount of oxygen ions to the reference electrode layer. Therefore, the oxygen sensor element in this system functions properly without suffering from mechanical failure by the action of an excessively high pressure of oxygen within the sensor element even when the engine continues to discharge exhaust gas high in the content of oxygen.

DETAILED DESCRIPTION OF THE INVENTION

Figures 1, 4:
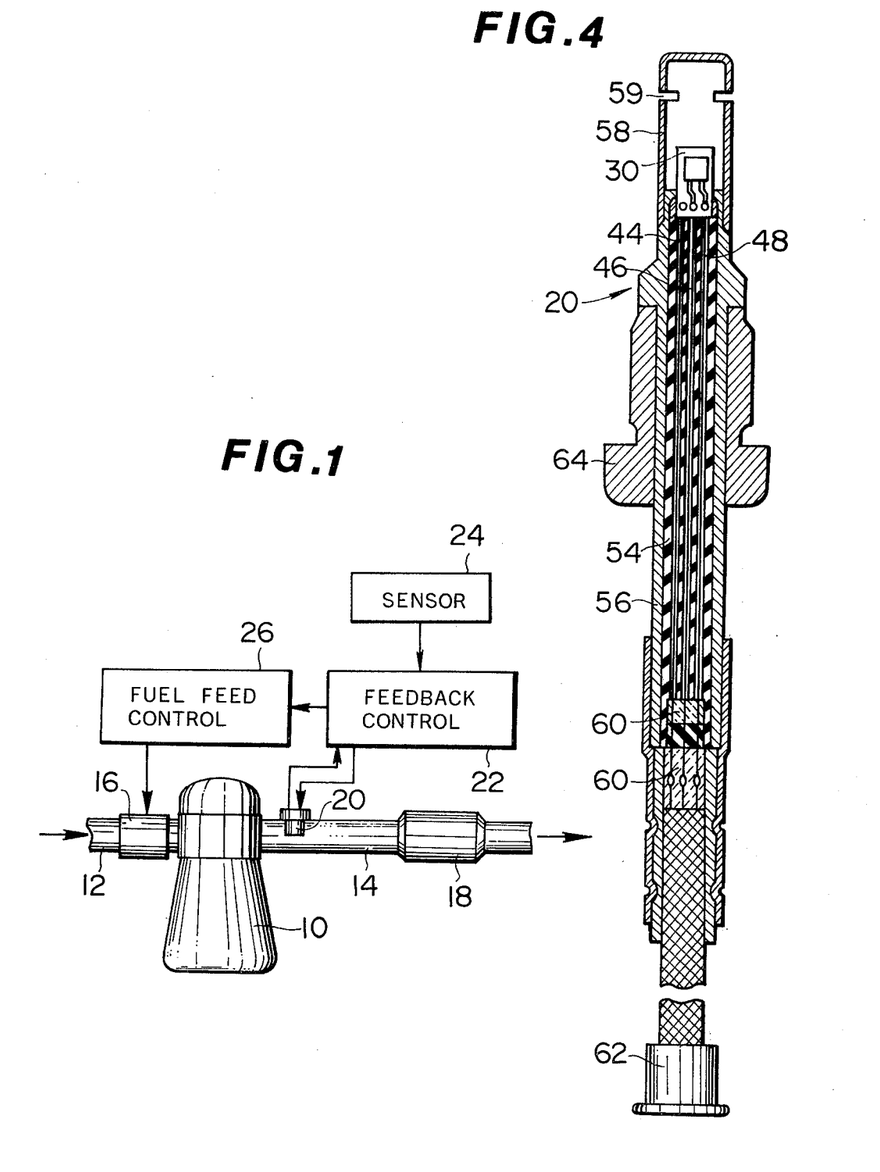
FIG. 1 is a diagrammatic presentation of an internal combustion engine system including an air/fuel ratio detection system according to the invention.
FIG. 4 is a longitudinal sectional view of an oxygen sensor which includes the sensor element of FIG. 2 and is so designed as to be useful in the exhaust system of automotive engines.

In FIG. 1, reference numeral 10 indicates an automotive internal combustion engine provided with an induction passage 12 and an exhaust passage 14. Indicated at 16 is an electrically controlled fuel-supplying apparatus such as electronically controlled fuel injection valves. A catalytic converter 18 that occupies a section of the exhaust passage 14 contains a conventional three-way catalyst by way of example.

To perform feedback control of the fuel-supplying apparatus 16 with the aim of supplying an optimum air-fuel mixture, in this case a stoichiometric mixture, to the engine 10 during its normal operation for thereby allowing the catalyst in the converter 18 to exhibit its best conversion efficiencies, an oxygen sensor 20 which serves as an air/fuel ratio detector is disposed in the exhaust passage at a section upstream of the catalytic converter 18. An electronic control unit 22 receives the output of the oxygen sensor 20 and provides a control signal to a control or drive element 26 of the fuel-supplying apparatus 16 based on deviations of the actual air/fuel ratio indicated by the output of the oxygen sensor 20 from the desired air/fuel ratio. As will be illustrated hereinafter, the oxygen sensor 20 has an oxygen-sensitive element of the type requiring the supply of a DC current thereto in order to produce and maintain a reference oxygen partial pressure therein, and an electric heater is provided to this element.

The air/fuel ratio control system in FIG. 1 includes a set of sensors 24 to detect selected parameters of the operating conditions of the engine 10. The control unit 22 utilizes the signals from these sensors 24 to judge whether the engine 10 is operating at high-load or at low- to medium-load and controls both the aforementioned DC current for the oxygen-sensitive element in the sensor 20 and a voltage to be applied to the heater in the same sensor 20 according to the load conditions of the operating engine 10. The particulars of the control unit 22 will later be described.

Figure 2:
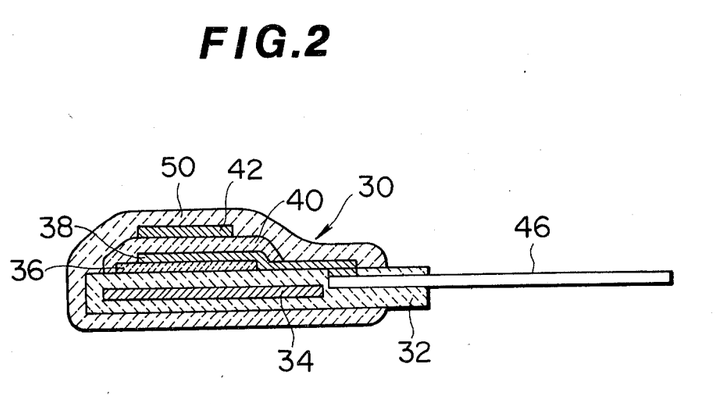
FIG. 2 is an explanatory sectional view of an oxygen sensor element used in the present invention.
Figure 3:
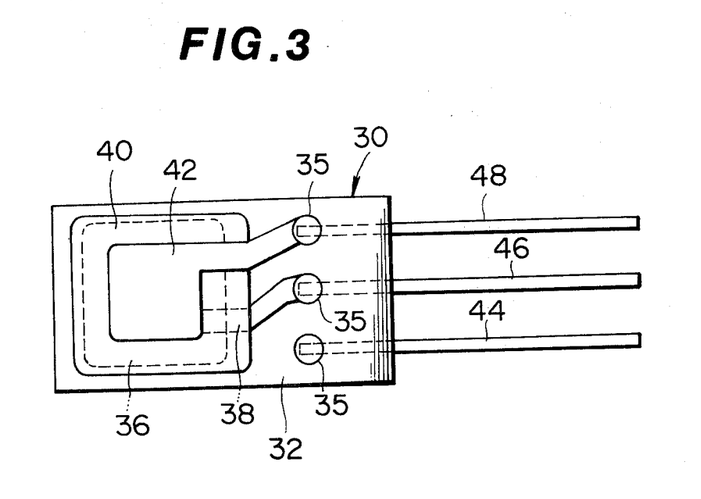
FIG. 3 is an explanatory plan view of the oxygen sensor element of FIG. 2.

FIGS. 2 and 3 show an exemplary oxygen-sensitive element 30 used in the oxygen sensor 20 in FIG. 1. A structurally basic member of this element 30 is a plate-shaped substrate 32 made of a ceramic material such as alumina. A heater 34 (omitted from illustration in FIG. 3) in the form of either a thin film-like layer or a thin wire of a suitable metal such as platinum is embedded in the substrate 32. It is a usual practice to prepare the substrate 32 by face-to-face bonding of two alumina sheets one of which is precedingly provided with the heater 34.

The sensitive part of this oxygen-sensitive element 30 takes the form of a laminate of thin layers supported on the ceramic substrate 32. The laminate includes a base layer 36 formed on a major surface of the substrate 32 so as to cover a sufficiently large area of the substrate surface. A ceramic material is used for this base layer 36. An inner electrode layer 38, which is often called reference electrode layer, lies on the upper surface of the base layer 36 so as to leave a marginal region of the surface of the base layer 36 uncovered. Platinum is a typical material for this electrode layer 38. A layer 40 of an oxygen ion conductive solid electrolyte such as zirconia containing a small amount of stabilizing oxide such as calcia or yttria closely covers the upper surfae of the inner electrode layer 38 and comes into direct contact with the marginal region of the base layer 36, so that the electrode layer 38 is substantially entirely enclosed by the base layer 36 and the solid electrolyte layer 40. The solid electrolyte layer 40 has a microscopically porous structure. An outer electrode layer 42, which is often called measurement electrode layer, lies on the upper surface of the solid electrolyte layer 40. The thus constructed laminate has a total thickness of about 70 microns for example.

This oxygen-sensitive element 30 has three lead wires 44, 46, 48, usually of platinum, which are inserted into the substrate 32 in their tip portions. The first lead wire 44 is connected to one terminal of the heater 34 within the substrate 32. The second lead wire 46 is connected to the inner or reference electrode layer 38 by using one of holes 35 formed in the upper half of the substrate 32 and a conductor filled in the hole 35. In a similar manner the third lead wire 48 is connected to the outer or measurement electrode layer 42, and this lead wire 48 is connected to the earth terminal of the heater 34 too. That is, the third lead wire 48 serves as a ground lead common to the heater 34 and an oxygen concentration cell constituted of the solid electrolyte layer 40 and the two electrode layers 38 and 42. The base layer 36 is not essential to the oxygen concentration cell, but this layer 36 is added for the purpose of enhancing the strength of adhesion of the laminated oxygen concentration cell to the ceramic substrate. Accordingly a preferable material for the base layer 36 is the same solid electrolyte material as the one used for the middle layer 40 of the concentration cell. The outer surfaces of the laminated sensitive part of this element 30 and a major part of the substrate 32 are covered with a porous protective layer 50 formed of a ceramic material such as calcium zirconate (in FIG. 3 the protective layer 50 is omitted from illustration for simplicity), so that a gas subject to measurement comes into contact with the measurement electrode layer 42 through the micropores in the protective coating layer 50.

FIG. 4 shows an exemplary construction of the oxygen sensor 20 which utilizes the oxygen-sensitive element 30 of FIG. 2 and is designed for attachment to the exhaust pipes or exhaust manifolds of automotive engines. In this sensor 20, the oxygen-sensitive element 30 is fixedly mounted on a forward end of a rod-shaped support 54 made of an insulating ceramic material such as mullite, and the three lead wires 44, 46, 48 of the element 30 are extended respectively through three axial holes (no numeral) bored in the ceramic rod 54, which is tightly fitted into a tubular case 56 of stainless steel. Through insulating seals 60 in the sensor, the lead wires 44, 46, 48 are connected to thicker and jacketed wires that extend to a suitable connector 62. A cup-shaped hood 58 of stainless steel is fixed to the forward end of the tubular case 56 so as to enclose the oxygen-sensitive element 30 therein. The side wall of the hood 58 is formed with apertures 59 to admit the exhaust gases into the interior of the hood 58, so that the oxygen-sensitive element 30 is exposed to the exhaust gases. To insert only the hooded end portion of the sensor 20 into an exhaust pipe and fix the sensor to a boss provided to the exhaust pipe, a threaded metal body 64 is fitted around the tubular case 56 in a region close to the hood 58.

To sense the concentration of oxygen in the exhaust gas by using this oxygen sensor 20 to thereby detect the air/fuel ratio of an air-fuel mixture actually supplied to the engine 10, it is necessary to produce and maintain a nearly constant partial pressure of oxygen within the oxygen-sensitive element 30. For this purpose a DC current of the order of $10^{-6}$ to $10^{-5}$ A is supplied from an external power source to the oxygen-sensitive element 30 by using the second and third lead wires 46 and 48 such that the current flows in the solid electrolyte layer 40 from the reference electrode layer 38 toward the measurement electrode layer 42. Besides, a suitable voltage is applied to the heater 34 from a seperate power source by using the first and third lead wires 44 and 48. The second lead wire 46 is used also to take out an electromotive force the oxygen-sensitive element 30 generates.

The flow of the DC current in the solid electrolyte layer 40 causes oxygen ions to migrate through the solid electrolyte layer from the measurement electrode layer 42 toward the reference electrode layer 38, and an increasing quantity of oxygen ions migrate in this way as the DC current is augmented. The oxygen ions arriving at the reference electrode layer 38 are converted to oxygen molecules, which gradually diffuse outwardly through the micropores in the solid electrolyte layer 40. Consequently an oxygen partial pressure of a nearly constant level determined by a balance between the inflow of oxygen ions and the outflow of oxygen molecules can be maintained at the interface between the solid electrolyte layer 40 and the reference electrode layer 38.

Prior to the description of preferred embodiments of the present invention, a previously proposed method of controlling the aforementioned current and the heater voltage for the above described oxygen-sensitive element 30 used in an air/fuel ratio control system of the type shown in FIG. 1 will be described with reference to FIGS. 5 and 6 in order to facilitate understanding of the effects of the present invention.

Figure 5:
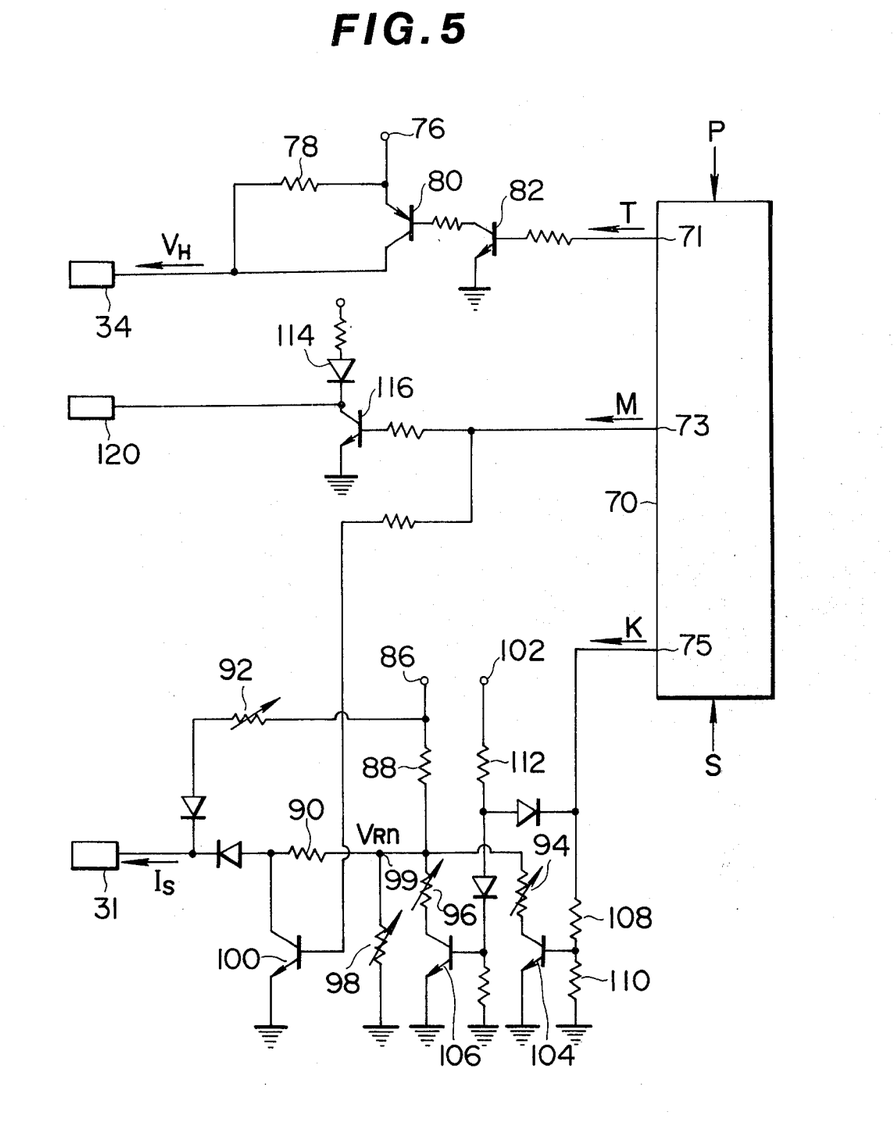
FIG. 5 is a circuit diagram showing a previously proposed current control circuit for operating the oxygen sensor element of FIG. 2 in the exhaust system of an automotive engine.

In the circuit diagram of FIG. 5 numeral 31 represents the concentration cell part of the oxygen-sensitive element 30, and the heater 34 in the same element 30 is indicated separately.

The circuit of FIG. 5 includes a control unit 70 which receives a signal or signals P representative of the operating conditions of the engine. For example, the signal P may represent the revolutions of the engine, pulse width of a fuel injection signal, flow rate of air taken into the engine, magnitude of intake vacuum and/or the degree of opening of the throttle valve. Based on such signal P, the control unit 70 continues to judge whether the engine is operating at high load above a predetermined level or at low- to medium load.

First output terminal 71 of the control unit 70 to put out a signal T for the control of a voltage applied to the heater 34 in the oxygen sensor is connected to the base of transistor 82. A DC power source 76 is connected to the heater 34 via a resistor 78 and a transistor 80 connected parallel to the resistor 78. The base of this transistor 80 is connected to the collector of the aforementioned transistor 82. During high-load operation of the engine the output T of the control unit 70 remains at high level to keep the transistor 82 conducting and, hence, the transistor 80 nonconducting. In this state the voltage $V_H$ supplied from the power source 76 to the heater 34 is limited by the resistor 78 so that the heater 34 exposed to high temperature exhaust gases produced under the high-load operating condition may generate only a limited amount of heat to thereby prevent excessive heating of the oxygen-sensitive element 30 as a whole. During medium- to low-load operation of the engine the output T of the control unit 70 remains at a very low level to keep the transistor 82 nonconducting, so that the transistor 80 becomes conducting. In this state the voltage $V_H$ supplied to the heater 34 augments since a portion of the voltage supplied from the power source 76 bypasses the resistor 78 via the transistor 80. Accordingly the heater 34 generates an increased amount of heat, so that the temperature of the oxygen-sensitive element 30 can be maintained at a level (e.g. above about 600° C.) high enough for its proper function despite a considerable lowering in the exhaust gas temperature during low-load operation of the engine.

To supply a small DC current $I_S$ to the concentration cell part 31 of the oxygen sensor, a constant DC power source 86 is connected to the lead wire 46 in FIGS. 1–3 via three resistors 88, 90 and 92 arranged in the illustrated manner. To keep a nearly constant oxygen partial pressure at the reference electrode layer 38 in the concentration cell part 31 of the oxygen sensor under varying operating conditions of the engine, the current $I_S$ is controlled because the rate of outward diffusion of oxygen molecules formed at the reference electrode layer 38 through the solid electrolyte layer 40 varies depending on the concentration of oxygen in the exhaust gas coming into contact with the measurement electrode layer 42 and the temperature of the exhaust gas. While the engine is operated with a lean mixture (meaning an air/fuel ratio below a stoichiometric ratio) the rate of the diffusion of oxygen molecules is relatively low because of a relatively high content of oxygen in the exhaust gas, and accordingly the current $I_S$ will be made relatively weak so as to adequately limit the inward migration of oxygen ions through the solid electrolyte layer 40. While the engine is operated with a fuel-rich mixture the current $I_S$ will be intensified to thereby promote the inward migration of oxygen ions so as to compensate for an increased rate of the diffusion of oxygen molecules into the exhaust gas which has become very low in the content of oxygen. Since the rate of the outward diffusion of oxygen molecules depends on the exhaust gas temperature too and becomes higher as the exhaust gas temperature becomes higher, the current control circuit of FIG. 5 is so designed as to increase the current $I_S$ stepwise as the load on the engine operating with a rich mixture becomes higher, as illustrated in FIG. 6.

In addition to the operating condition signal P, a signal S produced by the oxygen sensor in the exhaust gas is put into the control unit 70, and at second output terminal 73 the control unit 70 puts out a signal M which is produced by using the oxygen concentration signal S and indicates whether the engine is operating with a rich mixture or with a lean mixture. In the current control circuit there is a transistor 100 which grounds the resistor 90 when in the conducting state, and the base of this transistor 100 is connected to the output terminal 73 of the control unit 70. While the engine is operated with a rich mixture the output signal M at the terminal 73 of the control unit 70 becomes a high-level signal, so that the transistor 100 becomes nonconducting.

At third output terminal 75 the control unit 70 puts out a signal K which is produced by using the operating condition signal P and varies depending on the load on the operating engine. The current control circuit includes a resistor 96 which is connected in series with the aforementioned resistor 88 and is grounded when a transistor 106 is conducting, another resistor 98 which is connected to a junction point 99 between the resistors 88, 90 and 96 and grounded, and still another resistor 94 which is connected to the junction point 99 and grounded when a transistor 104 is conducting. A power source 102 is connected to the base of the transistor 106, and the output terminal 75 of the control unit 70 is connected to the base of the transistor 104 via a resistor 108 which is connected to another resistor 110 to provide a voltage divider. The power source 102 is connected to the resistor 108 too via a diode 112.

During low-load operation of the engine the signal K becomes a high-level signal so that the transistor 104 becomes conducting, while the voltage of the power source 102 is entirely used to keep the transistor 106 conducting because of the blocking function of the diode 112. In this state the voltage $V_c$ of the power source 86 is divided by the resistor 88 and a combined resistance provided by the three parallel-connected resistors 94, 96, 98 to give a voltage $V_{R1}$ at the junction point 99. Therefore, the current $I_S$ being supplied to the concentration cell part 31 of the oxygen sensor is given by the following equation (1).

$$I_S=(V_{R1}-V_S)/R_{90}+(V_C-V_S)/R_{92} \qquad (1)$$

where $V_S$ represents the output voltage of the oxygen-sensitive element 30 (31), and $R_{90}$ and $R_{92}$ represent the resistances of the resistors 90 and 92, respectively.

During medium-load operation of the engine the output K of the control unit 70 becomes a high impedance. Therefore, the voltage at the base of the transistor 104 becomes insufficient to keep this transistor 104 conducting, whereas the transistor 106 is still conducting by the action of the voltage supplied from the power source 102. Consequentially the resistor 94 becomes ineffective, and the voltage $V_c$ of the power source 86 is divided by the resistor 88 and a combined resistance of the two parallel-connected resistors 96 and 98 to give a voltage $V_{R2}$ at the junction point 99. In this state the current $I_S$ is given by substituting the voltage $V_{R2}$ for the voltage in the above equation (1). That is, the current $I_S$ is intensified by the difference of $V_{R2}$ from $V_{R1}$.

During high-load operation of the engine the output K of the control unit 70 becomes a low-level signal. Therefore, a portion of the voltage of the power source 102 is applied to the base of the transistor 104 through the diode 112, but the applied voltage is insufficient to render the transistor 104 conducting. The remaining portion of the voltage of the power source 102 acts on the base of the transistor 106 but is insufficient to keep this transistor 106 conducting. Since the transistor 106 becomes nonconducting, the voltage $V_c$ of the power source 86 is divided by the resistances of the two resistors 88 and 98 to give a voltage $V_{R3}$, which is greater than $V_{R2}$ under the medium-load condition, at the junction point 99. In this state the current $I_S$ is given by substituting the voltage $V_{R3}$ for the voltage $V_{R1}$ in the equation (1). That is, the current $I_S$ is further intensified from the intensified value under the medium-load condition, as shown in FIG. 6.

Figure 6:
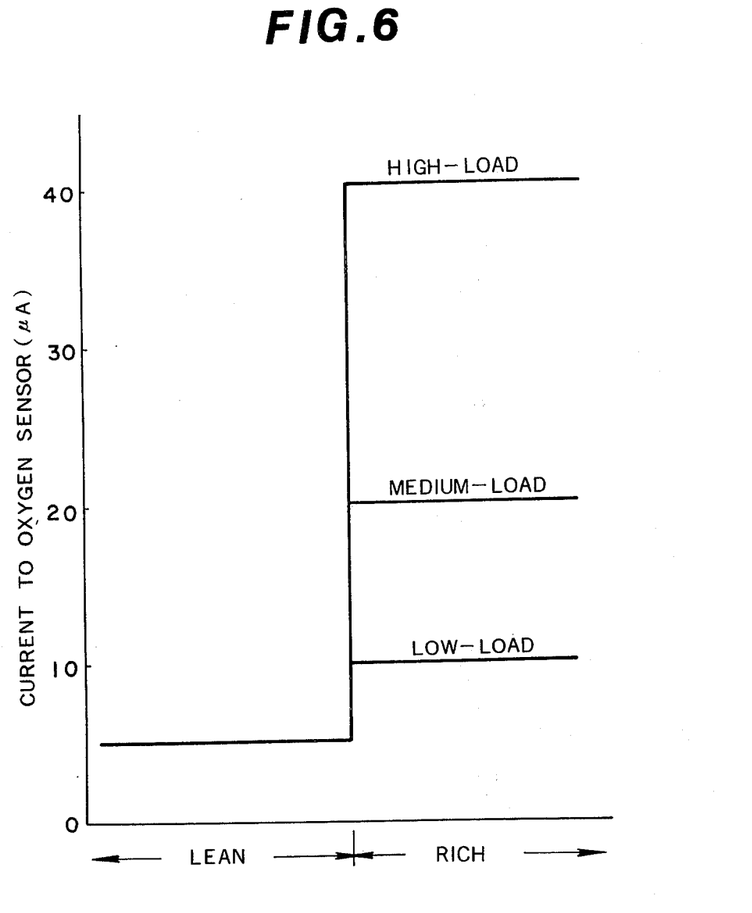
FIG. 6 is a chart showing the manner of controlling a current supplied to the oxygen sensor element by the control circuit of FIG. 5.

As can be seen in FIG. 6, while the engine is operated with a lean mixture the current control circuit of FIG. 5 keeps the current $I_S$ constantly at a very small value irrespective of the level of the load on the operating engine. Such a small value of the current $I_S$ is sufficient to maintain an adequate reference oxygen partial pressure in the oxygen-sensitive element 30 because of low rate of outward diffusion of oxygen molecules through the solid electrolyte layer 40 as mentioned hereinbefore. During operation of the engine with a lean mixture the output M of the control unit 70 remains as a low-level signal to render the transistor 100 conducting. Therefore, a current component given by $(V_{R1}-V_S)/R_{90}$ in the equation (1) becomes zero, so that the current $I_S$ becomes smaller and independent of the voltage $V_{R1}$, $V_{R2}$ or $V_{R3}$.

In FIG. 5 numeral 120 indicates a monitor lamp to indicate whether the engine is fed with a rich mixture or with a lean mixture. The power circuit for this lamp 120 includes a zenor diode 114 and a transistor 116 for grounding this circuit when desired. The output M of the control unit 70 is applied to the base of the transistor 116 so that the transistor 116 remains nonconducting to keep the lamp 120 lighting while the signal M is a high-level signal indicative of the feeding of a rich mixture to the engine.

Even when the engine is operated with a rich mixture the exhaust gas always contains a small amount of oxygen, and it suffices to supply a very small quantity of oxygen to the reference electrode 38 of the oxygen sensor element 30 for maintaining an adequate reference oxygen partial pressure. The required quantity of oxygen can be transferred to the reference electrode layer 38 by the action of the current $I_S$ even when it is weakened during low-load operation of the engine with the feed of a rich mixture.

In the exhaust gas, the concentration cell part 31 of the oxygen sensor generates an electromotive force of which the magnitude depends on the difference of the partial pressure of oxygen in the exhaust gas at the surface of the measurement electrode layer 42 and the reference oxygen partial pressure at the reference electrode layer 38. Therefore, the electromotive force becomes high when the engine is fed with a rich mixture to result in very small content of oxygen in the exhaust gas, and becomes low during feeding of a lean mixture to result in large content of oxygen in the exhaust gas. The electromotive force is taken out as the principal component of the sensor output S indicated in FIG. 5. Since the current $I_S$ flowing into the oxygen sensor element 30 is very weak (e.g. $10^{-6}$ to $10^{-5}$ A) compared with the electromotive force (e.g. about $10^{-1}$ V), the influence of the current $I_S$ on the output voltage of the oxygen sensor is negligibly small.

By the above described control method, the current $I_S$ is always kept flowing in the solid electrolyte layer 40 of the oxygen sensor element 30 from the reference electrode layer 38 toward the measurement electrode layer to continuously supply oxygen ions to the reference electrode layer 38, though the intensity of the current $I_S$ is varied in the above described manner. We have recognized that the continuous supply of the current $I_S$ in such a manner is unfavorable for the durability of the oxygen sensor element 30. More particularly, when the concentration of oxygen in the exhaust gas long remains at a high level as will be observed during long decelerating operation of the engine for example, the continuous inflow of oxygen ions to the reference electrode layer 38 is liable to produce an excessively high pressure of gaseous oxygen at or in the vicinity of the reference electrode layer 38 and sometimes causes peeling of the concentration cell part of the element 30 from the alumina substrate 32.

As described hereinbefore, an object of the present invention is to prevent excessive accumulation of oxygen at the reference electrode layer in the oxygen sensor element of the above described type during operation of the sensor element in the engine exhaust gases.

Figure 7:
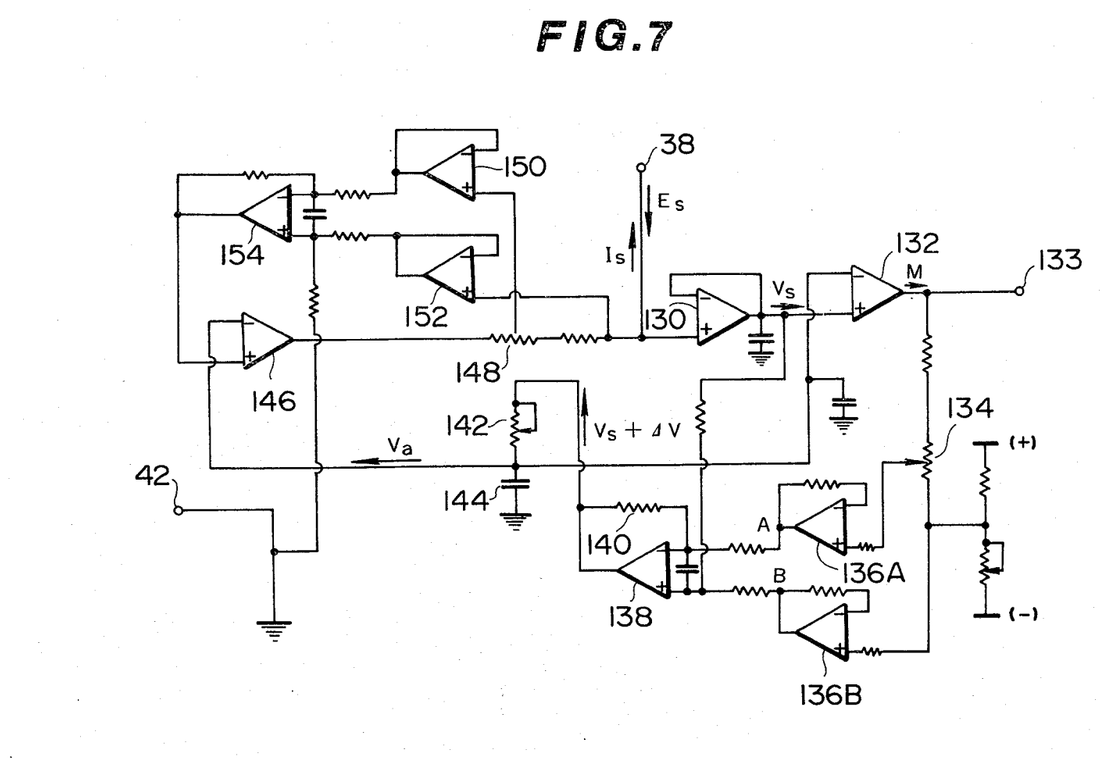
FIG. 7 is a circuit diagram showing an air/fuel ratio detection system embodying the present invention, using the oxygen sensor element of FIG. 2.

FIG. 7 shows a current control circuit embodying the present invention, as part of the control unit 22 in FIG. 1, for controlling the current $I_S$ supplied to the oxygen sensor element. In FIG. 7 the oxygen-sensitive element 30 of FIGS. 2 and 3 is represented by numeral 38 of the reference electrode layer and numeral 42 of the measurement electrode layer. Besides the circuit of FIG. 7, the control unit 22 includes a heater control circuit such as the one shown in FIG. 5 to control the voltage $V_H$ applied to the heater 34 in the oxygen-sensitive element 30.

In the circuit of FIG. 7, the output $E_S$ of the oxygen-sensitive element 30 is amplified in an amplifier 130 to give an output signal $V_S$. A comparator 132 makes a comparison between the voltage signal $V_S$ and a reference voltage to put out an air/fuel ratio signal M, which is a high-level signal while the engine is fed with a fuel-rich mixture but becomes a low-level signal when the engine is fed with a lean mixture. Indicated at 133 is an output terminal to transmit this signal M to another part of the control unit 22 for producing the control signal to be supplied to the element 26 of the fuel-supplying apparatus 16 in FIG. 1.

In FIG. 7, the air/fuel ratio signal M is put into an amplifier 136A via a portion of a voltage dividing resistor 134, and also to another amplifier 136B via the entire portion of the resistor 134. The amplified output voltage A of the amplifier 136A is put into the negative input terminal of a feedback amplifier 138, and the amplified output voltage B of the amplifier 136B is put into the positive input terminal of the feedback amplifier 138. In addition, the output voltage $V_S$ of the amplifier 130 for treating the sensor output $E_S$ is put into the positive input terminal of this feedback amplifier 138. (For simplicity, the voltage $V_S$ will hereinafter be referred to as sensor output voltage.) The output of this amplifier 138 is subjected to feedback to the input terminals via a feedback resistor 140. Accordingly, the output of the feedback amplifier 138 becomes a voltage given by the addition of a definite voltage $\Delta V$ to the sensor output voltage $V_S$. The definite voltage $\Delta V$ is determined by the voltage difference produced by the voltage dividing resistor 134. The voltage $V_S + \Delta V$ is charged in a capacitor 144 through a resistor 142. By charging in the capacitor 144, the voltage $V_S + \Delta V$ is smoothed to a voltage $V_a$.

The definite voltage $\Delta V$ is defined by $\Delta V = B - A$, and the relationship between the voltages A and B changes depending on the level of the air/fuel ratio signal M. While the signal M is high-level signal that indicates feeding of a rich mixture to the engine the voltage A as the output of the amplifier 136A is greater than the voltage B as the output of the amplifier 136B, but while the signal M is a low-level signal (negative voltage) indicating feeding of a lean mixture to the engine the voltage A is below the voltage B. Accordingly the voltage $\Delta V$ is a negative voltage during feeding of a rich mixture to the engine but becomes a positive voltage during feeding of a lean mixture. Therefore, the smoothed voltage $V_a$ is expressed as $V_S - |\Delta V|$ during feeding of a rich mixture and as $V_S + |\Delta V|$ during feeding of a lean mixture. ($|\Delta V|$ means absolute value.) The sensor output voltage $V_S$ is a positive voltage during feeding of a rich mixture to the engine but becomes negative during feeding of a lean mixture, and the absolute value of the negative voltage $V_S$ is not always equal to the absolute value of the positive voltage $V_S$.

The smoothed voltage $V_a$ is supplied from the capacitor 144 to the negative input terminal of an operational amplifier 146 to produce the current $I_S$ to be supplied to the concentration cell part of the oxygen-sensitive element 30. The current $I_S$ produced by this operational amplifier 146 is proportional to the absolute value of the smoothed voltage $V_a$ and becomes a positive current when the voltage $V_a$ is negative relative to a potential at the ground terminal or measurement electrode layer 42 of the oxygen-sensitive element 30, but becomes a negative current when the voltage $V_a$ is positive relative to the potential at the measurement electrode layer 42. The current $I_S$ being positive means that the current $I_S$ flows into the oxygen concentration cell from the reference electrode layer 38 toward the measurement electrode layer 42 with the effect of forcing oxygen ions to migrate in the solid electrolyte layer 40 toward the reference electrode layer 38. On the contrary, the current $I_S$ being negative means that the current $I_S$ flows out of the concentration cell from the reference electrode layer 38 with the effect of allowing oxygen ions to migrate in the solid electrolyte layer 40 toward the measurement electrode layer 42.

Figure 9:
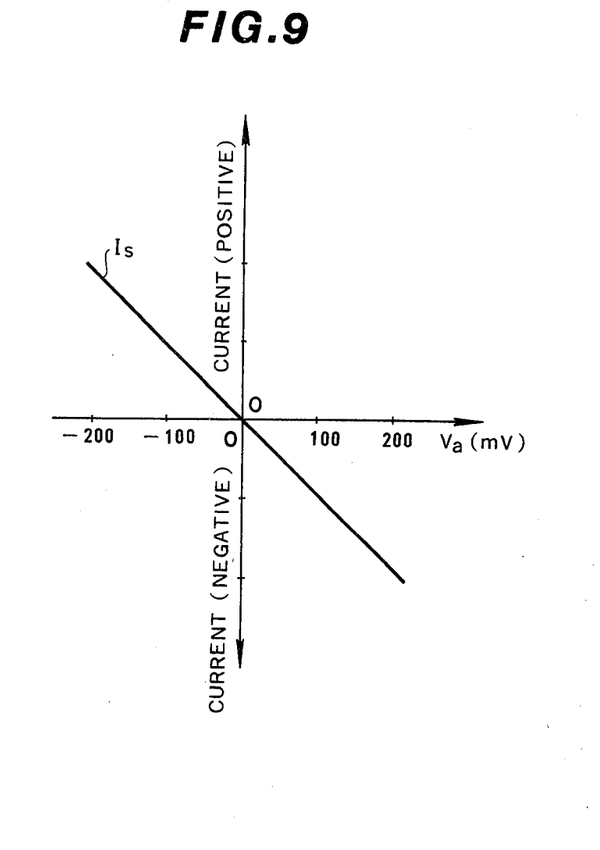
FIG. 9 is a graph showing the relationship between a smoothed voltage produced in the circuit of FIG. 7 and a current supplied from the same circuit to the oxygen sensor element.

In the circuit of FIG. 7, the current $I_S$ is made proportional to the smoothed voltage $V_a$ by using a voltage divider 148, combination of two amplifiers 150 and 152, and a differential amplifier 154. The current $I_S$ produced by the operational amplifier 146 flows through the voltage divider 148, and a voltage produced at a front part of the voltage divider 148 and another voltage produced at the rear end of the voltage divider 148 are put into the two amplifiers 150 and 152, respectively. The amplified output voltages of the two amplifiers 150, 152 are supplied to the differential amplifier 154, which amplifies the difference between the two input voltages and makes feedback of the amplified differential voltage of the operational amplifier 146. In this case, the constant of proportion K in the proportional relationship between the smoothed voltage $V_a$ and the current $I_S$ is determined so as to be smaller than zero but greater than $-1$, as can be seen in the graph of FIG. 9 for example.

Figure 8:
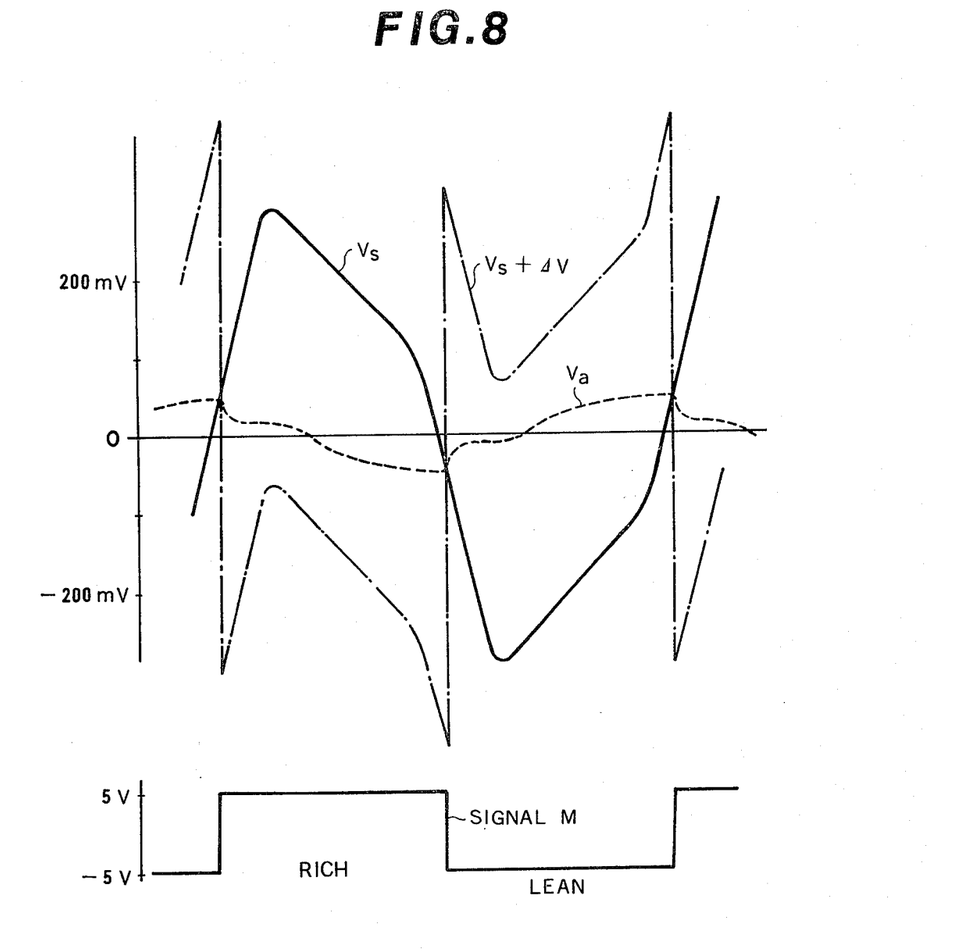
FIG. 8 is a chart illustrating the manner of function of a control circuit in FIG. 7.

The function of the current control circuit of FIG. 7 will be explained with reference to the chart of FIG. 8.

When the engine is alternately fed with a somewhat rich mixture and a somewhat lean mixture the sensor output voltage $V_S$ as the output of the amplifier 130 varies, for example, as represented by curve $V_S$. The air/fuel ratio signal M produced by the comparator 132 remains as a constant high-level signal during feeding of a rich mixture to the engine but shifts to a constant low-level signal during feeding of a lean mixture. Accordingly the output of the feedback amplifier 138 represented by the curve in chain line becomes a voltage given by the addition of a definite voltage $\Delta V$ to the sensor output voltage $V_S$, the voltage $\Delta V$ being negative during feeding of a rich mixture and positive during feeding of a lean mixture as explained hereinbefore. This voltage $V_S + \Delta V$ is smoothed by the capacitor 144 to a voltage $V_a$ represented by the curve in broken line. The smoothed voltage $V_a$ becomes negative during feeding of a rich mixture and becomes positive during feeding of a lean mixture.

While the smoothed voltage $V_a$ is negative, the operational amplifier 146 under the feedback from the differential amplifier 154 supplies a current $I_S$ that is positive and proportional to the smoothed voltage $V_s$ to the reference electrode 38 of the oxygen sensor element 30. While the smoothed voltage $V_a$ is positive, the current supplied from the operational amplifier 146 to the reference electrode 38 is negative and proportional to the absolute value of the smoothed voltage $V_a$, meaning that a positive current flows out of the reference electrode 38.

Since feedback control of the air/fuel ratio is continued based on the air/fuel ratio signal M, actual air/fuel ratio repeats to alternately become above and below the stoichiometric air/fuel ratio taken as the target of the feedback control. Therefore, a positive current and a negative current similar in absolute value are alternately and repeatedly supplied to the reference electrode 38 of the oxygen sensor element 30. Since oxygen ions migrate in the solid electrolyte layer 40 toward the reference electrode 38 when the positive current is applied to the reference electrode 38 but toward the measurement electrode 42 when the negative current is supplied, the alternate supply of the positive current and negative current to the reference electrode 38 is effective for prevention of excessive rise in the oxygen partial pressure at the reference electrode layer 38.

An average value of the output voltage $E_S$ or $V_S$ becomes smaller as the partial pressure of oxygen at the reference electrode layer 38 becomes lower. Then the smoothed voltage $V_a$ varies toward the negative side with the effect of increasing the current $I_S$ to increase the supply of oxygen ions to the reference electrode layer 38. Reversely, the smoothed voltage $V_a$ varies toward the positive side as the oxygen partial pressure at the reference electrode layer 38 becomes higher, and then the polarity of the current $I_S$ at the reference electrode 38 becomes negative to cause outflow of oxygen ions from this electrode 38. This means that the oxygen partial pressure at the reference electrode layer 38 is always controlled to a nearly constant level and therefore the output level of the oxygen sensor for a given concentration of oxygen in the exhaust gas remains constant during operation of the air/fuel ratio control system.

Figure 10:
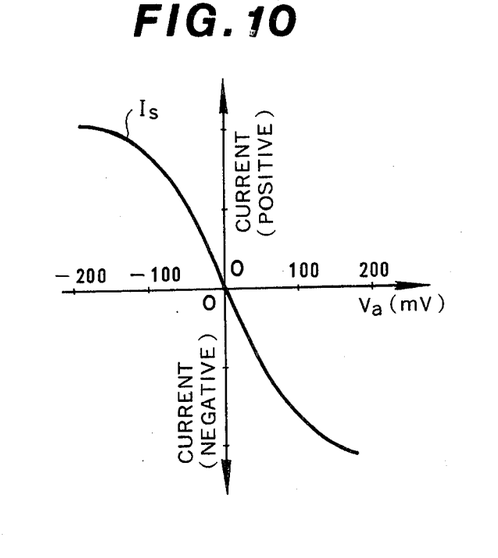
FIGS. 10 and 11 are graphs showing two different modifications of the voltage-current relationship shown in FIG. 9, respectively.
Figure 11:
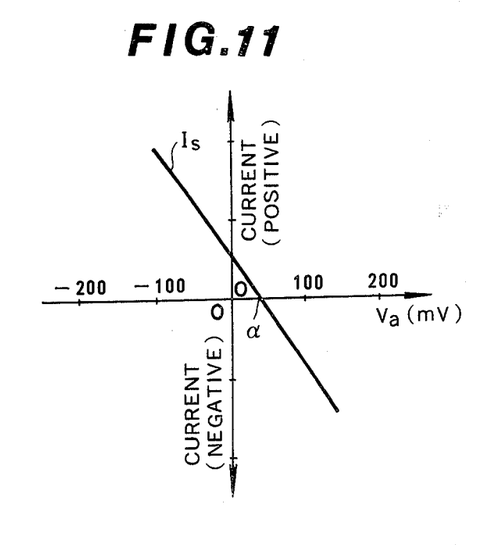

If desired the current control circuit of FIG. 7 may partly be modified such that the current $I_S$ varies as a quadratic function of the smoothed voltage $V_a$ as shown in FIG. 10 by way of example. It is also possible to modify the linear relationship between the smoothed voltage $V_a$ and the current $I_S$ in FIG. 9 in the manner as shown in FIG. 11. That is, the transition point of the current $I_S$ from positive to negative is shifted from the zero volt point of the smoothed voltage $V_a$ toward the positive side so that the current $I_S$ remains positive until the voltage $V_a$ becomes above a predetermined positive voltage $\alpha$. By this modification, the supply of oxygen ions to the reference electrode layer 38 is continued over an expanded range of the smoothed voltage $V_a$ or actual air/fuel ratio in the engine, and therefore the oxygen concentration at the reference electrode layer 38 can surely be maintained at a level slightly above zero level.

As a different modification, the combination of the amplifiers 136A, 136B and 138 in FIG. 7 may be changed to a circuit that produces a voltage by adding a constant negative voltage $-V_R$ to the sensor output voltage $V_S$ while the signal M indicates feeding of a rich mixture to the engine but adding a constant positive voltage $V_L$ to the sensor output voltage $V_s$ during feeding of a lean mixture and, in either case, averaging the voltage obtained by the addition.

The circuit of FIG. 7 is an analog circuit, but of course it is possible to alternatively employ a digital circuit to make a judgement about the actual air/fuel ratio, to produce the smoothed voltage $V_a$ and to vary the current $I_S$ in accordance with the foregoing description.

What is claimed is:

1. In a system for detecting the air/fuel ratio of air-fuel mixture supplied to an internal combustion engine, the system having an oxygen sensor element of the concentration cell type, which is disposed in an exhaust passage of the engine and has a laminate of a measurement electrode layer exposed to exhaust gas, a microscopically porous layer of an oxygen ion conductive solid electrolyte and a reference electrode layer supported on a ceramic substrate, current supplying means for supplying a DC current to the sensor element to cause migration of oxygen ions in the solid electrolyte layer to thereby produce a reference oxygen partial pressure at the interface between the solid electrolyte layer and the reference electrode layer, and judgement means for producing an air/fuel ratio signal which indicates whether the air/fuel ratio is above or below the stoichiometric ratio of said air-fuel mixture by comparing a signal voltage which is substantially proportional to output voltage of the sensor element with a reference signal, the improvement comprising said current supplying means comprising:

modification means for producing a modified voltage which is lower than said signal voltage by a predetermined value while said air-fuel ratio signal indicates that the air/fuel ratio is below said stoichiometric ratio but is higher than said signal voltage by said predetermined value while said air/fuel ratio signal indicates that the air/fuel ratio is above said stoichiometric ratio;

smoothing means for smoothing said modified voltage to produce a smoothed voltage; and current control means for controlling said DC current such that said DC current flows in said solid electrolyte layer from said reference electrode layer toward said measurement electrode layer and becomes smaller as said smoothed voltage becomes higher while said smoothed voltage is below a reference level, but flows in the reverse direction and becomes larger as said smoothed voltage becomes higher while said smoothed voltage is above said reference level.

2. A system according to claim 1, wherein said reference level is a potential at said measurement electrode layer in the sensor element.

3. A system according to claim 1, wherein said reference level is higher than a potential at said measurement electrode layer in the sensor element.

4. A system according to claim 1, wherein said DC current is controlled as a linear function of said smoothed voltage.

5. A system according to claim 1, wherein said DC current is controlled as a quadratic function of said smoothed voltage.

6. A system according to claim 1, wherein said current control means comprises an operational amplifier with an input terminal thereof connected to said smoothing means and an output terminal thereof connected to said reference electrode layer of the sensor element, said operational amplifier putting out a positive current which serves as said DC current while said smoothed voltage is below said reference level and putting out a negative current which serves as said DC current while said smoothed voltage is above said reference level.

7. A system according to claim 6, wherein said reference level is a potential at said measurement electrode layer of the sensor element.

8. A system according to claim 7, wherein said current control means further comprises a voltage divider connected between said operational amplifier and said reference electrode layer of the sensor to produce first and second voltages by using the output current of said operational amplifier, and a differential amplifier with an output terminal thereof connected to an input terminal of said operational amplifier for feedback of a voltage signal proportional to a difference between said first and second voltages.

9. A system according to claim 8, wherein said modification means comprises a voltage divider to produce third voltage and fourth voltage by using said air/fuel ratio signal, a feedback amplifier having a negative input terminal to receive a voltage proportional to said third voltage and a positive input terminal to receive both said signal voltage and a voltage proportional to said fourth voltage, and a capacitor connected to the output terminal of said differential amplifier via a resistance.

* * * * *

UNITED STATES PATENT AND TRADEMARK OFFICE
CERTIFICATE OF CORRECTION

PATENT NO. : 4,440,621
DATED : April 3, 1984
INVENTOR(S) : Tsuyoshi KITAHARA; Masaaki UCHIDA; Kohki SONE It is certified that error appears in the above-identified patent and that said Letters Patent is hereby corrected as shown below:

On the title page:

At item 30, kindly insert:

-- Foreign Application Priority Data --

-- Dec. 18, 1981 [JP]   Japan ..................... 56-204779 --

Signed and Sealed this

Fourth Day of September 1984

[SEAL]

Attest:

GERALD J. MOSSINGHOFF

*Attesting Officer*   *Commissioner of Patents and Trademarks*